US009405996B2

(12) United States Patent
Ionasec et al.

(10) Patent No.: US 9,405,996 B2
(45) Date of Patent: Aug. 2, 2016

(54) METHOD AND SYSTEM FOR GENERATING A PERSONALIZED ANATOMICAL HEART MODEL

(75) Inventors: Razvan Ionasec, Lawrenceville, NJ (US); Bogdan Georgescu, Plainsboro, NJ (US); Yefeng Zheng, Dayton, NJ (US); Dorin Comaniciu, Princeton Junction, NJ (US)

(73) Assignee: Siemens Aktiengesellschaft, Munich (DE)

( * ) Notice: Subject to any disclaimer, the term of this patent is extended or adjusted under 35 U.S.C. 154(b) by 1577 days.

(21) Appl. No.: 12/562,454

(22) Filed: Sep. 18, 2009

(65) Prior Publication Data

US 2010/0070249 A1 Mar. 18, 2010

Related U.S. Application Data

(60) Provisional application No. 61/097,966, filed on Sep. 18, 2008.

(51) Int. Cl.
*G06G 7/48* (2006.01)
*G06K 9/62* (2006.01)
*G06F 19/00* (2011.01)
*G06T 7/00* (2006.01)
*G06T 13/20* (2011.01)
*G06T 17/00* (2006.01)

(52) U.S. Cl.
CPC ............ *G06K 9/6256* (2013.01); *G06F 19/321* (2013.01); *G06F 19/3437* (2013.01); *G06T 7/0083* (2013.01); *G06T 7/0089* (2013.01); *G06T 13/20* (2013.01); *G06T 17/00* (2013.01); *G06K 2209/051* (2013.01); *G06T 2207/30048* (2013.01); *G06T 2210/41* (2013.01)

(58) Field of Classification Search
CPC . G06F 19/3437; G06F 19/321; G06K 9/6256; G06K 2209/051; G06T 7/0083; G06T 7/0089; G06T 13/20; G06T 17/00; G06T 2207/30048; G06T 2210/41
USPC ............................................................ 703/6
See application file for complete search history.

(56) References Cited

U.S. PATENT DOCUMENTS

| 7,117,026 B2 | 10/2006 | Shao et al. |
| 7,450,780 B2 | 11/2008 | Roche et al. |
| 2003/0109785 A1* | 6/2003 | Buck et al. .................... 600/437 |

(Continued)

OTHER PUBLICATIONS

Herbert Oertel et al., "Modelling the Human Cardiac Fluid Mechanics," third edition, May 28, 2009, Universitatsverlag Karlsruhe, downloaded from uvka.ubka.uni-karlsruhe.de/shop/download/1000011015, pp. 1-80.*

(Continued)

*Primary Examiner* — Kamini S Shah
*Assistant Examiner* — Russ Guill (57) ABSTRACT

A method and system for generating a patient specific anatomical heart model is disclosed. Volumetric image data, such as computed tomography (CT) or echocardiography image data, of a patient's cardiac region is received. Individual models for multiple heart components, such as the left ventricle (LV) endocardium, LV epicardium, right ventricle (RV), left atrium (LA), right atrium (RA), mitral valve, aortic valve, aorta, and pulmonary trunk, are estimated in said volumetric cardiac image data. A patient specific anatomical heart model is generated by integrating the individual models for each of the heart components.

20 Claims, 6 Drawing Sheets (56) References Cited

U.S. PATENT DOCUMENTS

| | | | |
|---|---|---|---|
| 2006/0004274 | A1 | 1/2006 | Hawman |
| 2006/0004275 | A1 | 1/2006 | Vija et al. |
| 2008/0101676 | A1 | 5/2008 | Zheng et al. |
| 2008/0262814 | A1 | 10/2008 | Zheng et al. |
| 2009/0123050 | A1 | 5/2009 | Ionasec et al. |
| 2009/0267941 | A1* | 10/2009 | Von Berg et al. ............. 345/423 |

OTHER PUBLICATIONS

Yefeng Zheng et al., "Fast automatic heart chamber segmentation from 3D CT data using marginal space learning and steerable features," Oct. 21, 2007, 2007 IEEE 11th International Conference on Computer Vision, eight unnumbered pages.*

T. Schenkel et al., "The Karlsruhe Heart Model KaHMo: a modular framework for numerical simulation of cardiac hemodynamics," Sep. 7, 2009, IFMBA Proceedings 25/IV, pp. 615-618.*

Chandrajait Bajaj et al., "Multi-component heart reconstruction from volumetric imaging," Jun. 2, 2008, Proceedings of the 2008 ACM symposium on Solid and physical modeling, pp. 193-202.*

Chandrajit Bajaj et al., "Patient specific heart models from high resolution CT," 2006, CompIMAGE Computational Modelling of Objects Represented in Images, pp. 1-6.*

Boyce E. Griffith et al., "An adaptive, formally second order accurate version of the immersed boundary method," 2007, Journal of Computational Physics, vol. 223, pp. 10-49.*

Yefeng Zheng et al. "Four-chamber heart modeling and automatic segmentation for 3-D cardiac CT volumes using marginal space learning and steerable features," Nov. 2008, IEEE Transactions on Medical Imaging, vol. 27, No. 11, pp. 1668-1681.*

Thomas J.R. Hughes et al., "Patient-specific mathematical models of the heart for simulation-based medical planning," Jul. 14, 2007, retrieved from the Wayback Machine dated Jul. 14, 2007, pp. 1-17.*

Hua Zhong et al., "Sensor guided ablation procedure of the left atrial endocardium," 2005, Medical Image Computing and Computer-Assisted Intervention MICCAI 2005, Springer-Verlag, pp. 1-8.*

W.P. Segars et al., "Enhanced 4D heart model based on high resolution dual source gated cardiac CT images," Nov. 3, 2007, 2007 IEEE Nuclear Science Symposium Conference Record, pp. 2617-2620.*

Martin Bertram et al., "Non-manifold mesh extraction from time-varying segmented volumes used for modeling a human heart," 2005, Eurographics-IEEE VGTC Symposium on Visualization, nine pages.*

Herbert Oertel et al., "Modelling the Human Cardiac Fluid Mechanics," second edition, 2006, Universitatsverlag Karlsruhe, pp. 1-39.*

David M. McQueen et al., "A three-dimensional computer model of the human heart for studying cardiac fluid dynamics," 2000, Computer Graphics, vol. 34, issue 1, pp. 56-60.*

Ingmar Voigt et al., "Model-driven physiological assessment of the mitral valve from 4D Tee," Mar. 2009, Medical Imaging 2009: Visualization, Image-Guided Procedures, and Modeling, Proceedings of the SPIE, vol. 7261, 11 pages.*

Ionasec, Razvan Ioan et al., "Dynamic Model-Driven Quantitative and Visual Evaluation of the Aortic Valve from 4D CT", Int'l Conference on Medical Image Computing and Computer-Assisted Intervention, 11(Pt 1), 2008.

Yang, Lin et al, "30 UltraSound Tracking of the Left Ventricles Using One-Step Forward Prediction and Data Fusion of Collaborative Trackers", CVPR, 2008.

Zheng, Yefeng, et al, "Four-Chamber Heart Modeling and Automatic Segmentation for 3D Cardiac CT Volumes Using Marginal Space Learning and Steerable Features", IEEE Transactions on Medical Imaging, 27(11), Nov. 2008.

* cited by examiner

Diastole      Systole

FIG. 5

METHOD AND SYSTEM FOR GENERATING A PERSONALIZED ANATOMICAL HEART MODEL

This application claims the benefit of U.S. Provisional Application No. 61/097,966, filed Sep. 18, 2008, the disclosure of which is herein incorporated by reference.

BACKGROUND OF THE INVENTION

The present invention relates to modeling the heart in medical images, and more particularly, to automatically estimating a personalized 4D anatomical heart model of the full cardiac system from volumetric image sequences (4D data).

Heart disease includes conditions affecting the heart, such as coronary heart disease, heart attack, congestive heart failure, heart valve disease and congenital heart disease. Heart disease is the leading cause of death for men and women in the United States. Mathematical models of the heart, such as statistical shape models, have the potential to reshape clinical evaluation and treatment of heart disease. However, conventional models of the heart have significant limitations, as they are typically either generic or restricted to specific substructures of the heart rather than modeling the full cardiac system. Accordingly, a method for generating a patient specific, personalized anatomic model of the full cardiac system is desirable.

BRIEF SUMMARY OF THE INVENTION

The present invention provides a method and system for generating a personalized anatomic model of the heart from volumetric image data. The personalized anatomical model can represent the full morphology, dynamics, and hemodynamics of the heart. Embodiments of the present invention utilize database-guided methods to estimate a 4D anatomical model including the four heart chambers, valves, and main vessels from volumetric data. Measurements based on the estimated model can be used together with certain physical and biomedical methods to simulate the blood flow as well as interaction between the blood and anatomical structures of the heart.

In one embodiment of the present invention, volumetric image data, such as computed tomography (CT), magnetic resonance imaging (MRI) or echocardiography image data, of a patient's cardiac region is received. Individual models for multiple heart components, such as the left ventricle (LV) endocardium, LV epicardium, right ventricle (RV), left atrium (LA), right atrium (RA), mitral valve, aortic valve, aorta, and pulmonary trunk, are estimated in said volumetric cardiac image data. A patient specific anatomical heart model is generated by integrating each individual heart components.

These and other advantages of the invention will be apparent to those of ordinary skill in the art by reference to the following detailed description and the accompanying drawings.

DETAILED DESCRIPTION

The present invention relates to generating a 4D personalized anatomical model of the heart from a sequence of volumetric data, such as computed tomography (CT), magnetic resonance imaging (MRI), and echocardiography data. Such sequences of volumetric data, also referred to herein as 4D image data or 4D images, are sequences taken over a period of time to cover one or more cardiac cycles, in which each frame is a 3D image (volume). Embodiments of the present invention are described herein to give a visual understanding of the heart modeling method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention are directed to generating a 4D personalized multi-scale anatomic model of the heart from volumetric image data. The personalized anatomical model can provide full morphology, dynamics, and hemodynamics of the heart. Embodiments of the present invention utilize database-guided methods to estimate a 4D anatomical model including the four heart chambers, valves, and main vessels from volumetric data. Measurements based on the estimated model can be used together with certain physical and biomedical methods to simulate the blood flow as well as interaction between the blood and anatomical structures of the heart.

Figure 1:
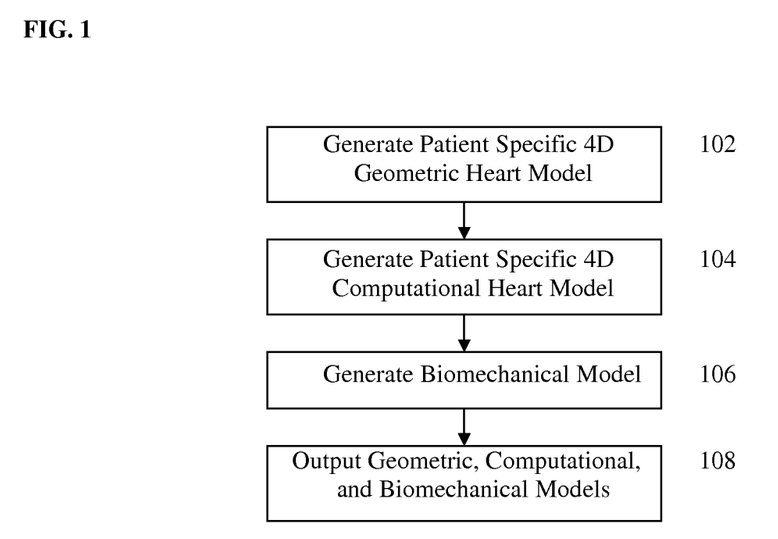
FIG. 1 illustrates a method for generating a 4D personalized multi-scale anatomical model of the heart according to an embodiment of the present invention.

FIG. 1 illustrates a method for generating a 4D personalized multi-scale anatomical model of the heart according to an embodiment of the present invention. The method of FIG. 1 transforms image data representing a coronary region of a patient to generate a personalized multi-scale anatomical model of the heart having morphological, dynamics, and hemodynamics model components. At step 102, a patient specific 4D geometric model estimated from a sequence of volumetric cardiac imaging data of a patient is generated. The sequence of volumetric image data can be a sequence of 3D images (volumes) acquired over a certain time period using at least one imaging modality, such as computer CT, MRI, or echocardiography. The 4D geometric model gives the morphology of the patient's heart and can be used to determine morphological (dimensions) and dynamic parameters for any component of the heart. For example, the patient specific 4D geometric model can be used to measure the left ventricle (LV) volume and ejection fraction (EF), inter-chamber synchronicity analysis, aortic and mitral valve analysis, etc. A method for generating the patient specific 4D geometric model is described in detail with reference to FIG. 2.

At step 104, a patient specific 4D computational model based on personalized geometry, material properties, fluid boundary conditions (pressure), and flow velocity measurements (e.g., velocity encoded contrast MR and echo Doppler) in the 4D geometric model is generated. For example, measurements of a chamber's volume and a valve's opening area computed over a full cardiac cycle enable for the characterization of the hemodynamics. Blood quantity, pressure and velocity can be directly estimated, for each of the four chambers, from the fitted 4D personalized anatomical heart model. The integration of Doppler echocardiogram or velocity encoded contrast MR velocity measurements further enhances the robustness of the blood parameter computation.

At step 106, a patient specific biomechanical model is generated based on Fluid Structure Interaction (FSI) simulations using the 4D computational model. A detailed simulation of the blood flow pattern of the patient, as well as the interaction of the blood with the anatomical structures of the heart, can be obtained by combining the above described measurements with established biomechanical and hemodynamics models, and finite element methods. For example, using FSI techniques the blood flow and tissue interaction can be simulated using the parameters measured in the computational model. This enables the computation of path, pressure, and velocity of the blood on a particle level with a desired granularity. If material properties are not measured in the computational model FSI can be specialized to computational fluid dynamics (CFD) in order to obtain full blood flow simulation using only the patient specific dynamic geometry, without simulating interaction of the blood and the tissue.

At step 108, the patient specific 4D multi-scale anatomic model including the 4D geometric heart model, the 4D computational model, and the biomechanical model is output. The 4D personalized multi-scale anatomical heart model can be output by storing the 4D personalized multi-scale anatomical heart model to a memory, storage, or computer readable medium. The 4D personalized multi-scale anatomical heart model can also be output by displaying the 4D personalized multi-scale anatomical heart model or printing images of the 4D personalized multi-scale anatomical heart model.

Figure 2:
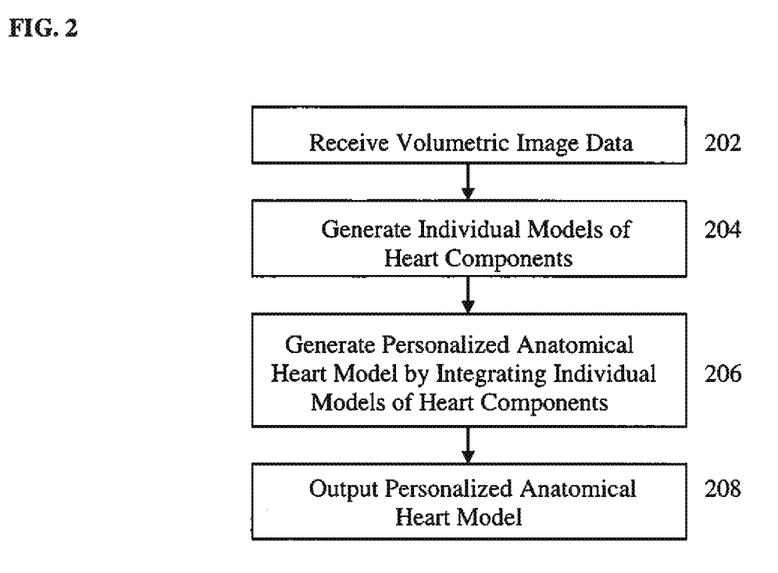
FIG. 2 illustrates a method for generating a 4D personalized geometric model of the heart according to an embodiment of the present invention.

FIG. 2 illustrates a method for generating a 4D personalized geometric model of the heart according to an embodiment of the present invention. The method of FIG. 1 transforms image data representing a coronary region of a patient to generate a personalized geometric model of the heart for that patient. At step 202, at least one sequence of volumetric image data is received. The sequence of volumetric image data can be a sequence of 3D images (volumes) acquired over a certain time period. For example, such a 4D image data (3D+time) can be acquired over a one full heart cycle. One or more sequences can be received using various medical imaging modalities. In one embodiment of the present invention, 4D CT data and 4D echocardiography data can be received. However, the present invention is not limited thereto, and other types of image data, such as 4D magnetic resonance (MR) image data can be received as well. The image data can be received directly from one or more image acquisition devices, such as a CT scanner and an ultrasound device. It is also possible that previously stored image data be loaded, for example from a memory or storage of a computer system or some other computer readable storage medium.

At step 204, an individual model is generated from the received image data for each of a plurality of heart components. According to an embodiment of the present invention, models are generated for the heart chambers: left ventricle (LV) (endocardium and epicardium), right ventricle (RV), left atrium (LA) and right atrium (RA); valves: mitral valve and aortic valve; and main vessels: aorta and pulmonary trunk. All of these portions of the heart are referred to herein collectively as the "heart components". For each heart component, a physiological model of the heart component is estimated in each frame of the 4D image data using a discriminative database-guide estimation/detection technique.

The physiological model of each anatomic structure (heart component) is constructed offline prior to generating the personalized heart model for a particular patient. Each physiological model is generated based on a mathematical representation of the corresponding heart component in a set of annotated training data. For example, the physiological model for each heart component can be generated using mean shapes of the heart component in a set of annotated training data. For example, United States Patent Application Publication No. 2008/0101676, which is incorporated herein by reference, describes a generating a four-chamber physiological heart model and fitting the heart model to image data. As described therein, the heart model is a 3D mesh and initial meshes for each chamber are generated using mean shapes of the chambers in annotated training data. Further, United States Patent Application No. 2009/0123050, which is incorporated herein by reference, describes a 4D physiological model of the aortic valve. A physiological model can similarly be generated offline for each of the heart components based on a set of annotated training data.

In order to estimate a physiological model of a particular heart component in a 3D image (i.e., frame of a 4D image sequence), the parameters of the physiological model are estimated to fit the image using a discriminative machine-learning technique based on a large database of annotated training images. According to one embodiment, marginal space learning (MSL) is used to localize the physiological model in each of the images.

The idea of MSL is not to learn a classifier directly in a full similarity transformation parameter space, but to incrementally learn discriminative classifiers in increasing dimensionality based on annotated training data. As the dimensionality increases, the valid (positive) space region becomes more restricted by previous marginal space classifiers. In order to estimate a physiological model of an anatomic structure, such as a particular heart component, in an image, the estimation of the similarity transformation (i.e., position, orientation, and scale) corresponding to the location of the heart component can be split into three stages: position estimation, position-orientation estimation, and full similarity transformation estimation. A discriminative classifier is trained for each stage based on the training data. All of the discriminative classifiers can be trained as Probabilistic Boosting Trees (PBTs). In addition to reducing the size of the search space, another advantage of MSL is that it is possible to use different features, such as 3D Haar features or steerable features to train the classifier in each marginal space level.

Examples of estimating physiological models of various heart components in 3D image data using MSL are described in the following publications, the disclosures of which are incorporated herein by reference: United States Patent Application Publication No. 2008/0101676, describes estimating a model for each chamber of the in 3D CT image data; United States Patent Application No. 2009/0123050, describes fitting a physiological model of the aortic valve to 4D CT data; and Yang et al., "3D Ultrasound Tracking of the Left Ventricles Using One-Step Forward Prediction and Data Fusion of Collaborative Trackers", CVPR 2008, describes fitting a model of the left ventricle to a sequence of 3D ultrasound images. It is to be understood that each of the heart components can be estimated by fitting a physiological model of the heart component to image data using discriminative machine-learning techniques, similarly to the above examples.

Once the parameters of each individual heart component model are estimated in each frame of the 4D image data, e.g., using MSL, learning-based boundary detection can be performed on the individual heart component model in each image to refine the estimated model parameters. In particular, the boundary of each estimated model can be refined using the learning-based boundary detection to increase the accuracy of the physiological model estimation for each heart component.

Figure 3:
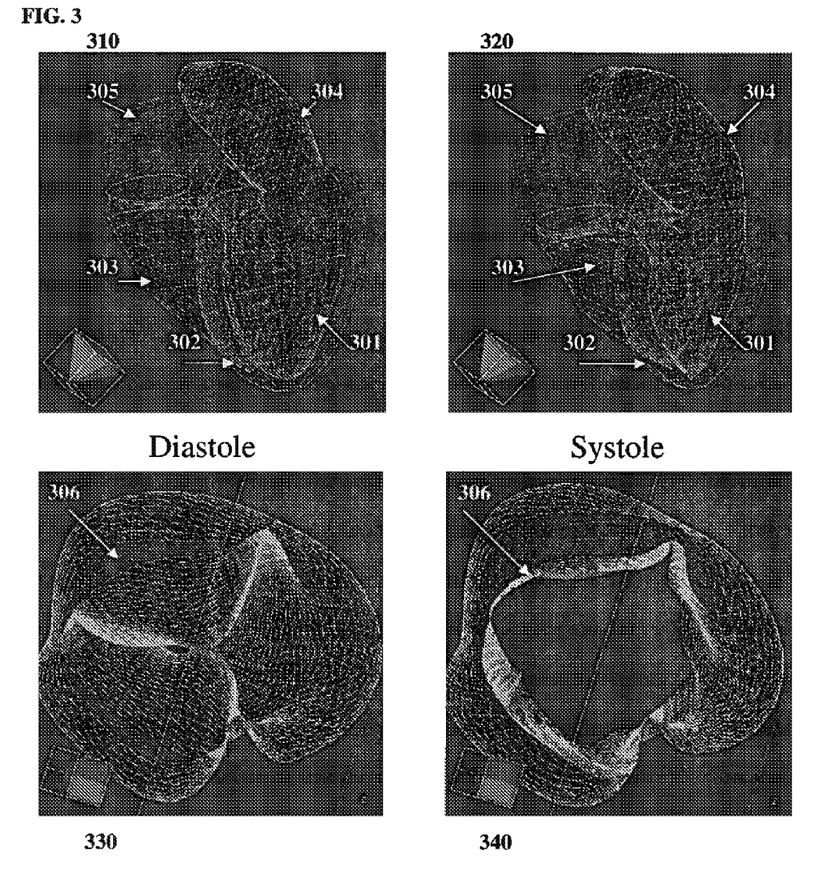
FIG. 3 illustrates exemplary models of the heart chambers and the aortic valve.

FIG. 3 illustrates exemplary models of the heart chambers and the aortic valve. As illustrated in FIG. 3 image 310 shows the LV endocardium 301, the LV epicardium 302, the RV 303, the LA 304, and the RA 305 in diastole and image 320 shows the LV endocardium 301, the LV epicardium 302, the RV 303, the LA 304, and the RA 305 in systole. Image 330 shows the aortic valve 306 in diastole and image 340 shows the aortic valve 306 in systole.

Returning to FIG. 2, at step 206, a 4D personalized anatomical model of the heart is generated by integrating the individual models generated for each of the heart components. Each of the individual heart component models resulting from step 104 is a mesh made of a certain number of points. According to an advantageous implementation, in order to integrate the individual models of the LV (endocardium and epicardium), RV, LA, RA, mitral valve, aortic valve, aorta, and pulmonary trunk, mesh point correspondences are established between connecting or overlapping models. The mesh point correspondences allow the models to be correctly aligned with respect to each other. It is possible to establish mesh point correspondence between models by re-sampling the models. For example, United States Patent Application Publication No. 2008/0262814, which is incorporated herein by reference, describes various re-sampling methods to establish mesh point correspondence between models of the four heart chambers in order to correctly align the heart chamber models. It is to be understood that the techniques described in United States Patent Application Publication No. 2008/0262814 can be extended to establish mesh point correspondence between the individual heart component models described herein.

Figure 4A:
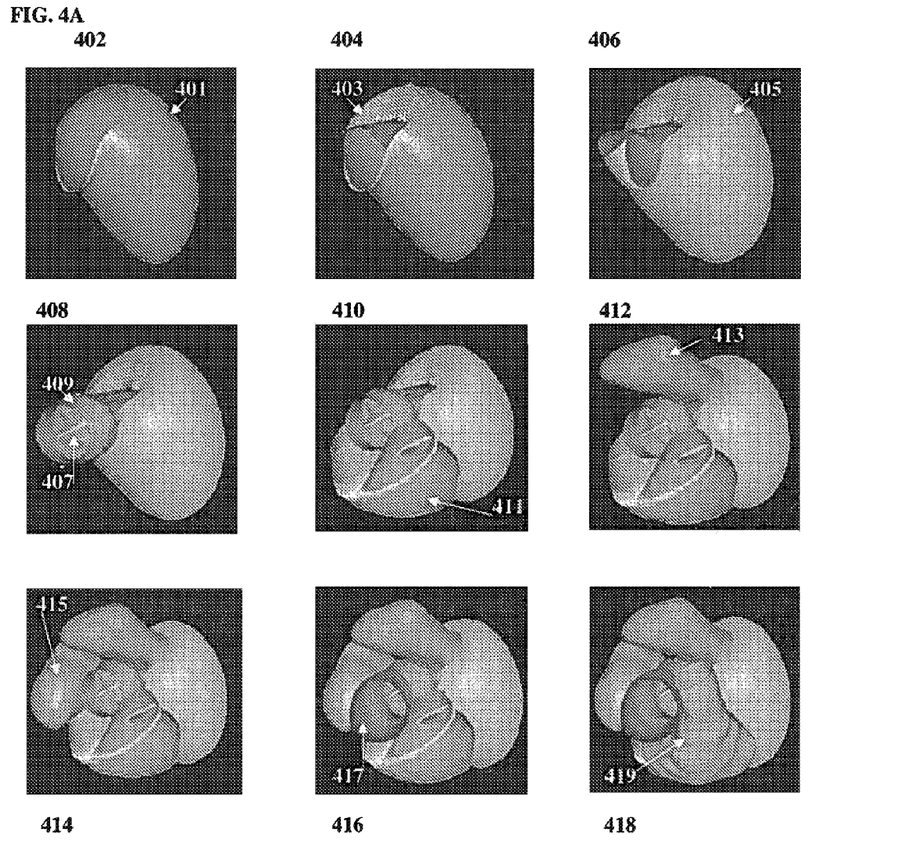
FIGS. 4A and 4B illustrate integrating individual models to generate a personalized anatomical heart model.
Figure 4B:
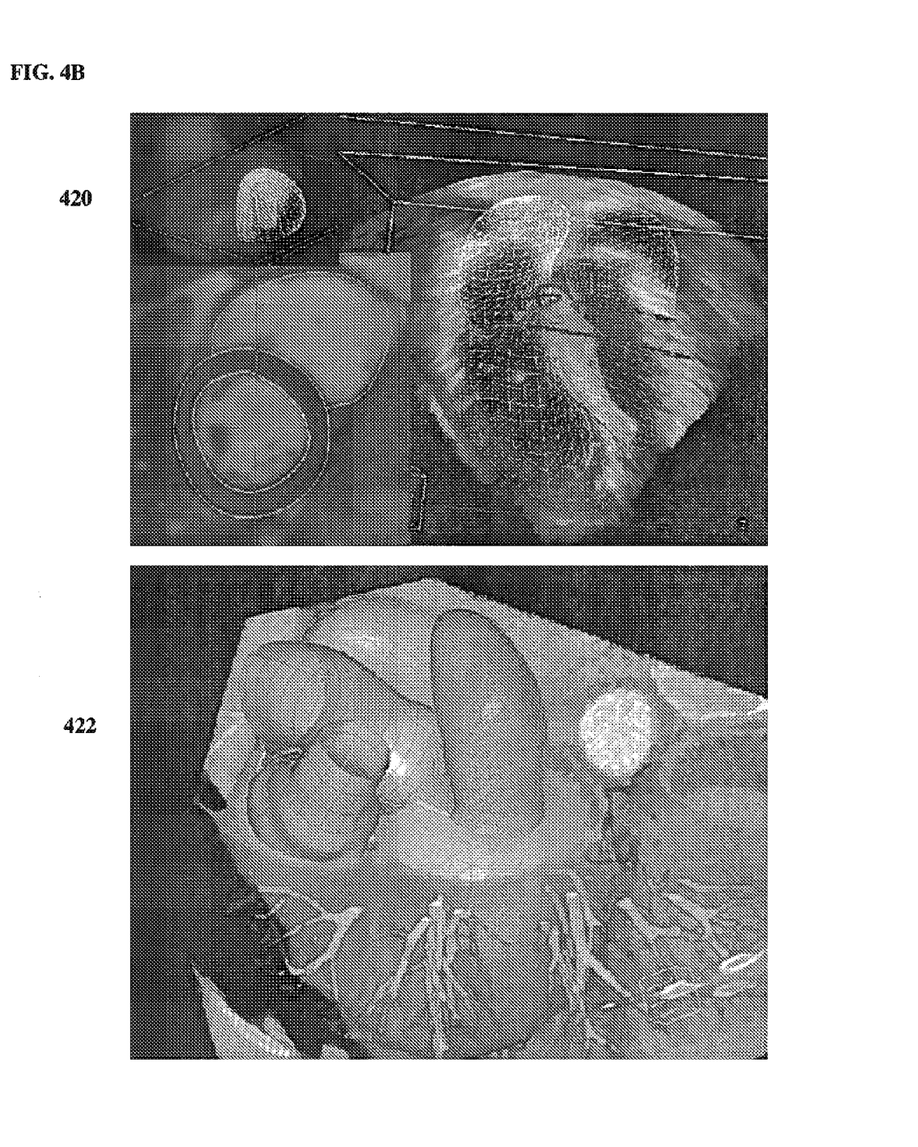

FIGS. 4A and 4B illustrate integrating individual models to generate a personalized anatomical heart model. The images of FIG. 4A illustrate a possible order for integrating the heart component models according to an embodiment of the present invention. As illustrated in FIG. 4A, image 402 shows an LV endocardium model 401. Image 404 shows the integration of the mitral valve model 403. Image 406 shows the integration of the LV epicardium model 405. Image 408 shows the integration of the aortic valve model 407 and the aortic root model 409. Image 410 shows the integration of the RV model 411. Image 412 shows the integration of the LA model 413. Image 414 shows the integration of the RA model 415. Image 416 shows the integration of the aorta model 417. Image 418 shows the integration of the pulmonary trunk model 419. As illustrated in FIG. 4B, images 420 and 422 show 3D renderings of the resulting personalized anatomical heart model fit to image data. It is to be understood that although FIGS. 4A and 4B, illustrate the integration of the heart component models for a 3D volume, the heart component models can be similarly integrated in each frame of a 4D image sequence.

Returning to FIG. 2, at step 208, the 4D personalized anatomical heart model is output. The 4D personalized anatomical heart model can be output by storing the 4D personalized anatomical heart model to a memory, storage, or computer readable medium. The 4D personalized anatomical heart model can also be output by displaying the 4D personalized anatomical heart model or printing an image of the 4D personalized anatomical heart model. The output 4D personalized anatomical heart model can be used for further medical image processing. For example, the 4D personalized anatomical heart model can be used to estimate various morphological and functional measurements, of the heart. The 4D personalized anatomic heart model can also be used to simulate blood flow or blood-tissue interaction.

Measurements of a chamber's volume and a valve's opening area computed over a full cardiac cycle enable for the characterization of the hemodynamics. Blood quantity, pressure and velocity can be directly estimated, for each of the four chambers, from the fitted 4D personalized anatomical heart model. The integration of Doppler echocardiogram velocity measurements further enhances the robustness of the blood parameter computation. These measurements result in the generation of the patient specific 4D computation model.

A detailed simulation of the blood flow pattern of the patient, as well as the interaction of the blood with the anatomical structures of the heart, can be obtained by combining the above described measurements with established biomechanical and hemodynamics models, and finite element methods. This enables the computation of path, pressure, and velocity of the blood on a particle level with a desired granularity. Such simulation results in the generation of the patient specific biomechanical model.

The patient specific geometric, computational, and biomechanical models can have significant applications in disease prediction, such as thrombosis analysis. For example, the main drawback of commonly used mechanical prosthetic valves is their propensity for hemolysis and thrombus formation. Clinical reports indicate that such artificial heart valves are still unable to eliminate the problems of thrombosis and anticoagulant complications. The high shear stresses generated in the blood flow causes red blood cell and platelet damages, which eventually lead to thrombosis. If the so-called Kolmogorov turbulent eddies are smaller than or similar in size to the blood cells, they then directly interact with and transfer energy to the cells, thus damaging their membranes. The personalized anatomical heart model generated as described above, according to an embodiment of the present invention, can be used to characterize the fluid structure interaction and to track blood particles during the cardiac cycle. This enables thrombosis analysis and disease prediction, which can be used to provide significant support in the design of personalized prosthetic valves to provide optimal hemodynamics.

The structural, functional and hemodynamics information given by the 4D personalized anatomical model of the cardiac system, described above, can also provide new methods for stroke and heart attack prevention caused by embolus. The detection and tracking of thrombus formation, as well as the predication of the embolus detach can be achieved using the morphological and hemodynamics measurements obtained from the cardiac model.

Figure 5:
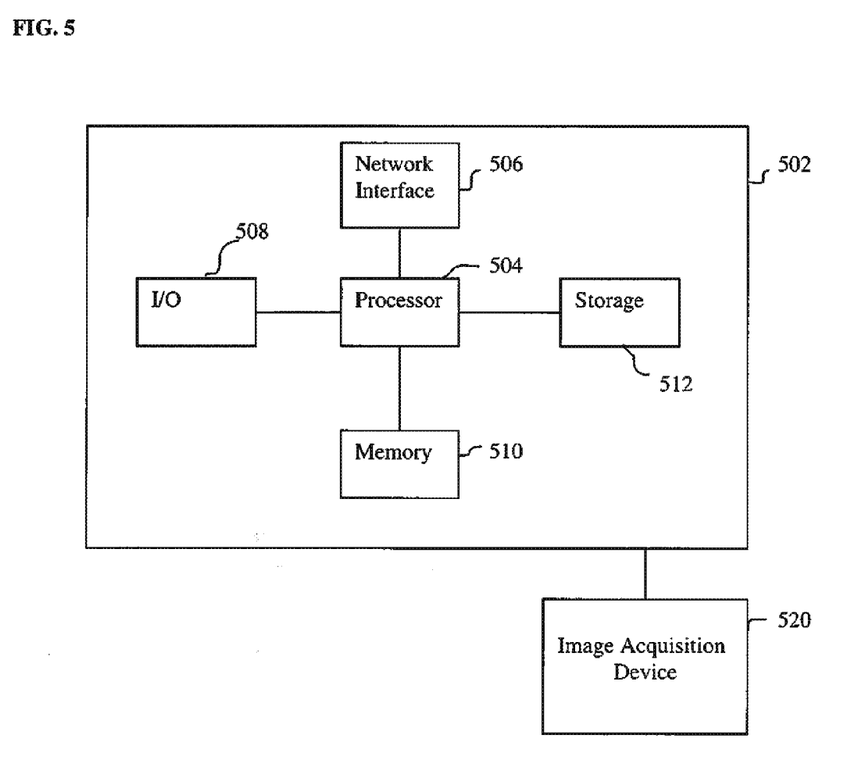
FIG. 5 is a high-level block diagram of a computer capable of implementing the present invention.

The above-described methods for generating a personalized anatomic model of the heart may be implemented on a computer using well-known computer processors, memory units, storage devices, computer software, and other components. A high-level block diagram of such a computer is illustrated in FIG. 5. Computer 502 contains a processor 504, which controls the overall operation of the computer 502 by executing computer program instructions which define such operation. The computer program instructions may be stored in a storage device 512 (e.g., magnetic disk) and loaded into memory 510 when execution of the computer program instructions is desired. Thus, the steps of the method of FIGS. 1 and 2 may be defined by the computer program instructions stored in the memory 510 and/or storage 512 and controlled by the processor 504 executing the computer program instructions. At least one image acquisition device 520, such as a CT scanning device, ultrasound device, etc., can be connected to the computer 502 to input the 3D volumes to the computer 502. It is possible to implement the image acquisition device 520 and the computer 502 as one device. It is also possible that the image acquisition device 520 and the computer 502 communicate wirelessly through a network. The computer 502 also includes one or more network interfaces 506 for communicating with other devices via a network. The computer 502 also includes other input/output devices 508 that enable user interaction with the computer 502 (e.g., display, keyboard, mouse, speakers, buttons, etc.). Such input/output devices 508 may be used in conjunction with a set of computer programs as an annotation tool to annotate volumes received from the image acquisition device 520. One skilled in the art will recognize that an implementation of an actual computer could contain other components as well, and that FIG. 5 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

What is claimed is:

1. A method for generating a patient specific four-dimensional (4D) multi-scale anatomical heart model having morphological, dynamics, and hemodynamics model components, comprising:
   generating a patient specific 4D geometric model estimated from a sequence of volumetric cardiac imaging data of a patient generated using at least one medical imaging modality by:
      receiving at least one sequence of volumetric cardiac imaging data of the patient generated using the at least one medical imaging modality,
      estimating individual 4D models for a plurality of heart components in said at least one sequence of volumetric cardiac imaging data, the plurality of heart components including a plurality of heart chambers and a plurality of heart valves, and
      generating a patient specific 4D geometrical heart model by integrating the individual 4D models for each of said plurality of heart components;
   generating a patient specific 4D computational model based at least on measurements of volumes of the heart chambers and measurements of opening areas of the heart valves in the 4D geometric model by:
      computing the measurements of the volumes of the heart chambers and the measurements of the opening areas of the heart valves in the 4D geometric model over a full cardiac cycle, wherein the measurements of the opening areas of the heart valves are measured directly from the heart valves in the 4D geometric model, and
      estimating blood quantity, pressure, and velocity, for each of the heart chambers based on the measurements of the volumes of the heart chambers and the measurements of the opening areas of the heart valves in the 4D geometric model; and
   generating a patient specific biomechanical model based on Fluid Structure Interaction (FSI) simulations using the 4D computational model.

2. The method of claim 1, further comprising:
   determining morphological and dynamic parameters for any of a plurality of heart components based on the 4D geometric heart model.

3. The method of claim 2, further comprising:
   determining at least one dynamical mechanical parameter based on the 4D computational model.

4. The method of claim 3, wherein said at least one dynamical mechanical parameter comprises strain.

5. The method of claim 2, further comprising:
   determining at least one hemodynamic parameter based on the biomechanical model.

6. The method of claim 5, wherein said at least one hemodynamic parameter comprises at least one of wall shear stress, compliance and stiffness, turbulence intensity, dilation pressure, and full heart blood velocity patterns.

7. The method of claim 1, wherein said step of receiving at least one sequence of volumetric cardiac imaging data of the patient generated using at least one medical imaging modality comprises:
   receiving at least one of a 4D computed tomography (CT) image sequence and a 4D echocardiography image sequence, and a 4D magnetic resonance imaging (MRI) sequence.

8. The method of claim 1, wherein said step of estimating individual 4D models for a plurality of heart components in said at least one sequence of volumetric cardiac imaging data comprises:
   estimating models of a left ventricle (LV) endocardium, LV epicardium, right ventricle (RV), left atrium (LA), right atrium (RA), mitral valve, aortic valve, aorta, and pulmonary trunk.

9. The method of claim 8, wherein said step of generating a patient specific 4D geometrical heart model by integrating the individual 4D models for each of said plurality of heart components comprises:
   generating the patient specific 4D geometric heart model by sequentially integrating the individual 4D models of the LV endocardium, the mitral valve, the LV epicardium, the aortic valve and the aortic root, the RV, the LA, the RA, the aorta, and the pulmonary trunk model, in that order.

10. The method of claim 1, wherein said step of estimating individual 4D models for a plurality of heart components in said at least one sequence of volumetric cardiac imaging data comprises:
    fitting a physiological model of each of said plurality of heart components to said volumetric cardiac imaging data using discriminative machine-learning based estimation.

11. The method of claim 10, wherein the physiological model of each heart component is generated based on a mathematical representation of the heart component in a set of annotated training data.

12. The method of claim 10, wherein said step of fitting a physiological model of each of said plurality of heart components to said volumetric cardiac imaging data using discriminative machine-learning based estimation comprises:
    estimating a position, orientation, and scale of the physiological model of each of said plurality of heart components in said volumetric cardiac imaging data using marginal space learning (MSL) with discriminative classifiers trained based on annotated training data.

13. The method of claim 12, wherein said step of estimating individual 4D models for a plurality of heart components in said at least one sequence of volumetric cardiac imaging data further comprises:
refining the estimated physiological model of each of said plurality of heart components in said volumetric cardiac imaging data using learning-based boundary detection.

14. The method of claim 1, wherein said step of generating a patient specific 4D geometrical heart model by integrating the individual 4D models for each of said plurality of heart components comprises:
establishing mesh point correspondence between connecting ones of the individual models.

15. The method of claim 14, wherein establishing mesh point correspondence between connecting ones of the individual models comprises:
establishing mesh point correspondence between connecting ones of the individual models for the heart chambers; and
establishing mesh point correspondence between the individual models for the heart chambers connecting ones of the individual models for the heart valves.

16. The method of claim 1, wherein:
said step of estimating individual 4D models for a plurality of heart components in said at least one sequence of cardiac volumes comprises estimating an individual model for each of said plurality of heart components in each frame of the at least one sequence of volumetric cardiac imaging data; and
said step of generating a patient specific 4D geometrical heart model by integrating the individual 4D models for each of said plurality of heart components comprises generating a patient specific geometrical heart model in each frame of the at least one sequence of volumetric cardiac imaging data.

17. The method of claim 1, wherein said sequence of volumetric cardiac imaging data is generated over at least one heart cycle.

18. The method of claim 1, wherein said step of generating a patient specific 4D computational model based at least on measurements of volumes of the heart chambers and opening areas of the heart valves in the 4D geometric model comprises:
generating the patient specific 4D computational model further based on one or more of personalized geometry, material properties, fluid boundary conditions, and flow velocity measurements in the 4D geometric model.

19. An apparatus for generating a patient specific four-dimensional (4D) multi-scale anatomical heart model having morphological, dynamics, and hemodynamics model components, comprising:
a processor; and
a memory storing computer program instructions, which when executed by the processor cause the processor to perform operations comprising:
generating a patient specific 4D geometric model estimated from a sequence of volumetric cardiac imaging data of a patient generated using at least one medical imaging modality by:
receiving at least one sequence of volumetric cardiac imaging data of a patient generated using at least one medical imaging modality,
estimating individual 4D models for a plurality of heart components in said at least one sequence of volumetric cardiac imaging data, the plurality of heart components including a plurality of heart chambers and a plurality of heart valves, and
generating a patient specific 4D geometrical heart model by integrating the individual models for each of said plurality of heart components;
generating a patient specific 4D computational model based at least on measurements of volumes of the heart chambers and measurements of opening areas of the heart valves in the 4D geometric model by:
computing the measurements of the volumes of the heart chambers and the measurements of the opening areas of the heart valves in the 4D geometric model over a full cardiac cycle, wherein the measurements of the opening areas of the heart valves are measured directly from the heart valves in the 4D geometric model, and
estimating blood quantity, pressure, and velocity, for each of the heart chambers based on the measurements of the volumes of the heart chambers and the measurements of the opening areas of the heart valves in the 4D geometric model; and
generating a patient specific biomechanical model based on Fluid Structure Interaction (FSI) simulations using the 4D computational model.

20. A non-transitory computer readable medium encoded with computer executable instructions for generating a patient specific four-dimensional (4D) multi-scale anatomical heart model having morphological, dynamics, and hemodynamics model components, the computer executable instructions defining steps comprising:
generating a patient specific 4D geometric model estimated from a sequence of volumetric cardiac imaging data of a patient generated using at least one medical imaging modality by:
receiving at least one sequence of volumetric cardiac imaging data of the patient generated using the at least one medical imaging modality,
estimating individual 4D models for a plurality of heart components in said at least one sequence of volumetric cardiac imaging data, the plurality of heart components including a plurality of heart chambers and a plurality of heart valves, and
generating a patient specific 4D geometrical heart model by integrating the individual models for each of said plurality of heart components;
generating a patient specific 4D computational model based at least on measurements of volumes of the heart chambers and measurements of opening areas of the heart valves in the 4D geometric model by:
computing the measurements of the volumes of the heart chambers and the measurements of the opening areas of the heart valves in the 4D geometric model over a full cardiac cycle, wherein the measurements of the opening areas of the heart valves are measured directly from the heart valves in the 4D geometric model, and
estimating blood quantity, pressure, and velocity, for each of the heart chambers based on the measurements of the volumes of the heart chambers and the measurements of the opening areas of the heart valves in the 4D geometric model; and
generating a patient specific biomechanical model based on Fluid Structure Interaction (FSI) simulations using the 4D computational model.

* * * * *